(12) United States Patent
Thomas et al.

(10) Patent No.: US 10,932,788 B2
(45) Date of Patent: Mar. 2, 2021

(54) LIGATION CLIP WITH LATCHING AND RETENTION FEATURES

(71) Applicant: Covidien LP, Mansfield, MA (US)

(72) Inventors: Justin Thomas, New Haven, CT (US); Eric Brown, Haddam, CT (US); Jacob C. Baril, Norwalk, CT (US); Gregory R. Morck, Middletown, CT (US); Roy J. Pilletere, North Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 116 days.

(21) Appl. No.: 16/261,662

(22) Filed: Jan. 30, 2019

(65) Prior Publication Data

US 2019/0314026 A1    Oct. 17, 2019

Related U.S. Application Data

(60) Provisional application No. 62/655,882, filed on Apr. 11, 2018.

(51) Int. Cl.
*A61B 17/122*    (2006.01)

(52) U.S. Cl.
CPC ................. *A61B 17/122* (2013.01)

(58) Field of Classification Search
CPC ... A61B 17/122; A61B 17/1227; A61B 17/28; A61B 17/1285; A61B 17/1225; A61B 17/1222; A61M 39/284; A61M 39/286
See application file for complete search history.

(56) References Cited

U.S. PATENT DOCUMENTS

| | | | |
|---|---|---|---|
| 2,668,538 | A | 2/1954 | Baker |
| 3,439,523 | A | 4/1969 | Wood |
| 3,713,533 | A | 1/1973 | Reimels |
| 4,076,120 | A | 2/1978 | Carroll et al. |
| 4,146,130 | A | 3/1979 | Samuels et al. |
| 4,187,712 | A | 2/1980 | Samuels et al. |
| 4,212,303 | A | 7/1980 | Nolan |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

European Search Report dated Jul. 17, 2019, issued in European Appln. No. 19168518.

*Primary Examiner* — George J Ulsh
*Assistant Examiner* — Andrew P. Restaino
(74) *Attorney, Agent, or Firm* — Carter, DeLuca & Farrell LLP

(57) ABSTRACT

A surgical ligation clip includes a first jaw, a second jaw, and a hinge portion that pivotably couples the first jaw to the second jaw. The first and second jaws define respective clamping surfaces and include locking elements. The clamping surfaces support retention structure that minimizes movement of the clamp about tissue when the ligation clip is in the clamped position. The locking elements are supported on the first and second jaws and are movable into engagement with each other to retain the ligation clip in the clamped position.

14 Claims, 10 Drawing Sheets

(56) References Cited

U.S. PATENT DOCUMENTS

| | | |
|---|---|---|
| 4,212,390 A | 7/1980 | Raczkowski et al. |
| 4,294,355 A | 10/1981 | Jewusiak et al. |
| 4,344,531 A | 8/1982 | Giersch |
| 4,346,869 A | 8/1982 | MacNeill |
| 4,361,229 A | 11/1982 | Mericle |
| 4,390,019 A | 6/1983 | Leveen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,391,035 B1 | 5/2002 | Appleby et al. |
| 6,419,682 B1 | 7/2002 | Appleby et al. |
| 6,421,920 B1 | 7/2002 | Jensen |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,220,507 B1 * | 12/2015 | Patel .................... A61B 17/064 |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santini et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 2002/0046961 A1 | 4/2002 | Levinson et al. |
| 2002/0177863 A1 | 11/2002 | Mandel et al. |
| 2004/0199178 A1 | 10/2004 | Small |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1 | 7/2009 | Whiting |
| 2011/0224700 A1 | 9/2011 | Schmidt et al. |
| 2011/0295291 A1 | 12/2011 | Trivisani |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro |
| 2013/0261642 A1 | 10/2013 | Willett et al. |
| 2014/0054192 A1 | 2/2014 | Chancibot |
| 2014/0243862 A1 | 8/2014 | Bagaoisan et al. |
| 2014/0276970 A1 | 9/2014 | Messerly et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |

FOREIGN PATENT DOCUMENTS

| | | |
|---|---|---|
| CN | 106264647 A | 1/2017 |
| DE | 10116168 A1 | 11/2001 |
| GB | 2353710 A | 3/2001 |

* cited by examiner

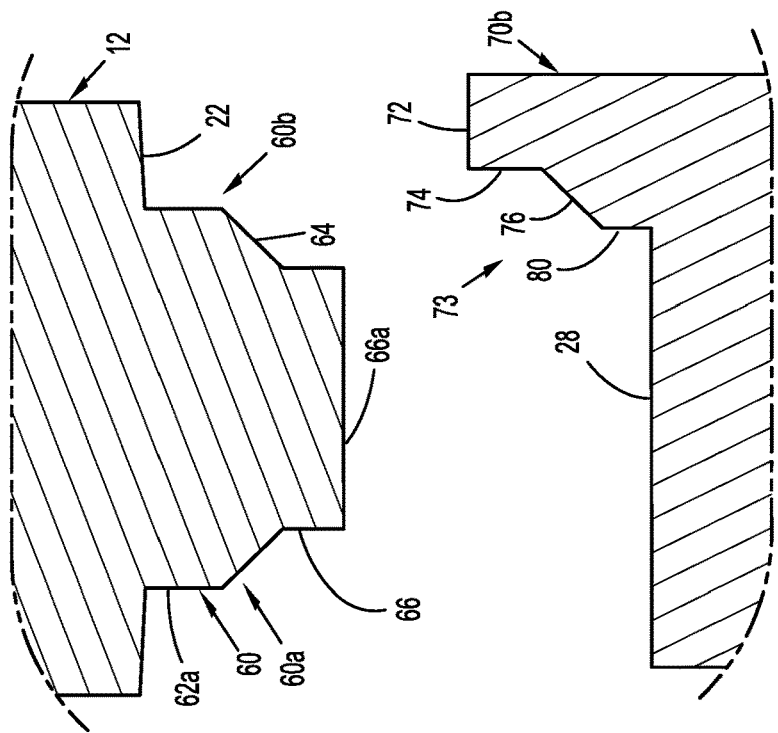
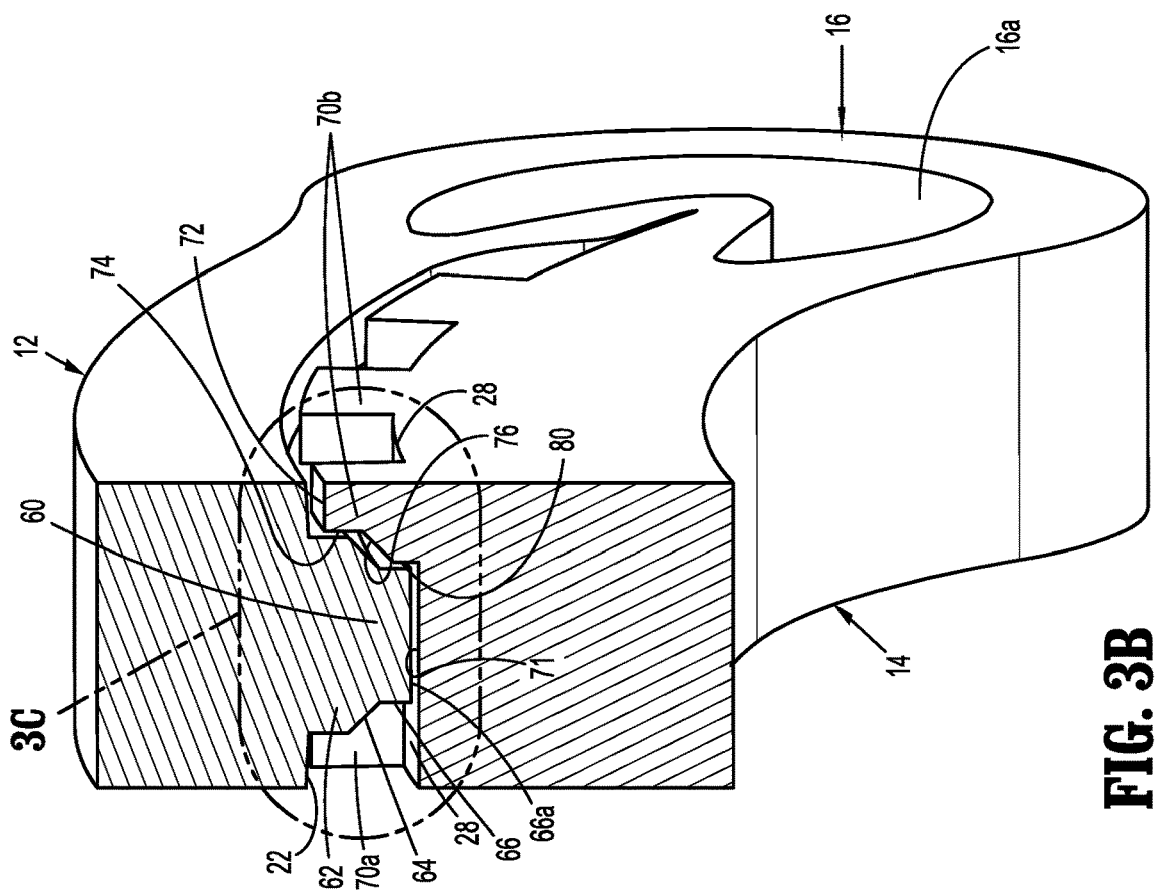

LIGATION CLIP WITH LATCHING AND RETENTION FEATURES

CROSS-REFERENCE TO RELATED APPLICATION

This application claims the benefit of and priority to U.S. Provisional Patent Application No. 62/655,882 filed Apr. 11, 2018, the entire disclosure of which is incorporated by reference herein.

BACKGROUND

1. Technical Description

The present disclosure is directed to ligation clips for sealing body vessels and, more particularly, to polymeric ligation clips that include latching structure and tissue retention features for securely clamping the ligation clip about a body vessel.

2. Background of Related Art

Ligation clips are well known in the surgical arts and are commonly used during a variety of surgical procedures to ligate tissue, e.g., a body vessel. Typically, ligation clips include first and second jaws that include clamping surfaces. The jaws are pivotably connected to each other and movable between open and clamped positions. When the ligation clip is clamped about tissue, the tissue is compressed between the clamping surfaces of the first and second jaws. Typically, the jaws of the ligation clip include a latching mechanism to retain the ligation clip in the clamped position about tissue and retention structure positioned on the clamping surfaces of the jaws to prevent the clamped ligation clip from moving in relation to the tissue. Any movement of the clamped ligation clip in relation to the tissue may have a negative impact on the performance of the ligation clip.

Ligation clips can be formed of polymeric materials. In current polymeric clip designs, pre-compressing the ligation clip or closing the ligation clip may deform latching mechanism such that the reliability of the latching mechanism is impaired. The loss of the ability to maintain the ligation clip in the clamped position about a body vessel may result in movement of the ligation clip in relation to the body vessel or disengagement of the ligation clip from the body vessel.

A continuing need exists in the art for a ligation clip with improved latching structure and retention characteristics to more effectively retain the ligation clip in a clamped position about tissue.

SUMMARY

One aspect of the disclosure is directed to a ligation clip including a first jaw and a second jaw. The first jaw defines a first clamping surface and supports a stepped longitudinal rib. The stepped longitudinal rib extends along at least a portion of the length of the first clamping surface and includes opposite side walls. Each of the opposite side walls includes an angled wall portion. The second jaw defines a second clamping surface and is pivotably supported in relation to the first jaw to facilitate movement of the ligation clip from an open position to a clamped position. The second jaw has a first row of protrusions supported on one side of the second clamping surface and a second row of protrusions supported on an opposite side of the second clamping surface. Each of the protrusions of the first and second rows of protrusions has an inner side wall that is in opposition to the stepped longitudinal rib when the ligation clip is in the clamped position. The inner side wall of each of the protrusions includes an angled wall portion. The first row of protrusions is laterally spaced from the second row of protrusions to define a channel that extends longitudinally between the first and second rows of protrusions and is positioned to receive the stepped longitudinal rib when the ligation clip is in the clamped position. The angled wall portion of the opposite side walls of the stepped longitudinal rib and the angled side wall portion of the protrusions of the first and second rows of protrusions are positioned to be in opposition to each other in the clamped position of the ligation clip.

In embodiments, the protrusions in the first row of protrusions are longitudinally aligned and spaced from each other and the protrusions in the second row of protrusions are longitudinally aligned and spaced from each other.

In some embodiments, each of the opposite side walls of the stepped longitudinal rib includes a first vertical side wall portion that has a first end contiguous with the first clamping surface and a second end contiguous with the angled wall portion, and each of the protrusions of the first and second rows of protrusions includes a first vertical wall portion having a first end contiguous with the second clamping surface and a second end contiguous with the angled wall portion, wherein the first vertical side wall of the opposite side walls of the stepped longitudinal rib are in opposition to the first vertical wall portions of the protrusions when the ligation clip is in a clamped position.

In certain embodiments, the stepped longitudinal rib includes a second vertical side wall portion that has a first end contiguous with the first clamping surface and a second end contiguous with the angled wall portion, and the inner side wall of each of the protrusions includes a vertical wall portion having a first end contiguous with the second clamping surface and a second end contiguous with the angled wall portion, wherein the second vertical side wall portions of the stepped longitudinal rib are in opposition to the second vertical wall portions of the protrusions when the ligation clip is in a clamped position.

In embodiments, each of the protrusions in the first row of protrusions is longitudinally offset from the each of protrusions in the second row of protrusions such that the protrusions are alternatingly positioned on opposite sides of the second clamping surface along the length of the second clamping surface.

In some embodiments, the first jaw includes a first locking element and the second jaw includes a second locking element, wherein the first locking element is movable into engagement with the second locking element to retain the ligation clip in the clamped position.

In certain embodiments, the first or second locking element includes a head including a first side wall defining a first notch, and the other of the first or second locking element includes a box-like structure defining a through bore having a first locking tab extending into the through bore, wherein the first locking tab is positioned to be received within the first notch of the head to retain the ligation clip in the clamped position.

In embodiments, the head includes a second side wall defining a second notch and the box-like structure includes a second locking tab that extends into the through bore, wherein the second locking tab is positioned to be received within the second notch of the head to retain the ligation clip in the clamped position.

In some embodiments, the first notch and the first locking tab have triangular configurations.

In certain embodiments, the box-like structure is rectangular in shape and is defined by angled side walls and a radiused proximal wall that are configured to guide the head into the through bore of the box-like structure.

In embodiments, the head has a rectangular cross-sectional shape and the through bore is configured to receive the head.

In some embodiments, the box-like structure has an open distal end.

In certain embodiments, the first or second locking element includes a head supporting a stop member that extends outwardly of the head, and the other of the first or second locking element includes a box-like structure that defines a through bore. The stop member is deformable to facilitate passage of the stop member through the through bore during movement of the ligation clip from the open position to the closed position. The stop member is configured in an undeformed state to engage the box-like structure to obstruct movement of the ligation clip from the clamped position to the open position.

In embodiments, the head includes a hooked portion and the other one of the first and second locking elements includes an engagement portion, wherein the hooked portion is positioned to engage the engagement portion to retain the ligation clip in the clamped position.

Another aspect of the present disclosure is directed to a ligation clip that includes a first jaw and a second jaw. The first jaw defines a first clamping surface and includes a first locking element and the second jaw defines a second clamping surface and includes a second locking element. The second jaw is pivotably supported in relation to the first jaw to facilitate movement of the ligation clip from an open position to a clamped position. The first locking element includes a head having a first side wall defining a first notch and the second locking element includes a box-like structure defining a through bore having a first locking tab extending into the through bore. The first locking tab is positioned to be received within the first notch of the head to retain the ligation clip in the clamped position.

In embodiments, the head includes a second side wall defining a second notch and the box-like structure includes a second locking tab that extends into the through bore. The second locking tab is positioned to be received within the second notch of the head to retain the ligation clip in the clamped position.

Yet another aspect of the present disclosure is directed to a ligation clip that includes a first jaw and a second jaw. The first jaw defines a first clamping surface and includes a first locking element, and the second jaw defines a second clamping surface and includes a second locking element. The second jaw is pivotably supported in relation to the first jaw to facilitate movement of the ligation clip from an open position to a clamped position. The first locking element includes a head supporting a stop member that extends outwardly of the head. The second locking element includes a box-like structure that defines a through bore. The stop member is deformable to facilitate passage of the stop member through the through bore during movement of the ligation clip from the open position to the clamped position. The stop member is configured in an undeformed state to engage the box-like structure to obstruct movement of the ligation clip from the clamped position to the open position.

BRIEF DESCRIPTION OF THE DRAWINGS

Various exemplary embodiments of the presently disclosed ligation clip are described herein below with reference to the drawings, wherein:

FIG. 3B is a cross-sectional view taken along section line 3B-3B of FIG. 3;

FIG. 3C an enlarged view of the indicated area of detail shown in FIG. 3B;

DETAILED DESCRIPTION OF EMBODIMENTS

Figure 1A:
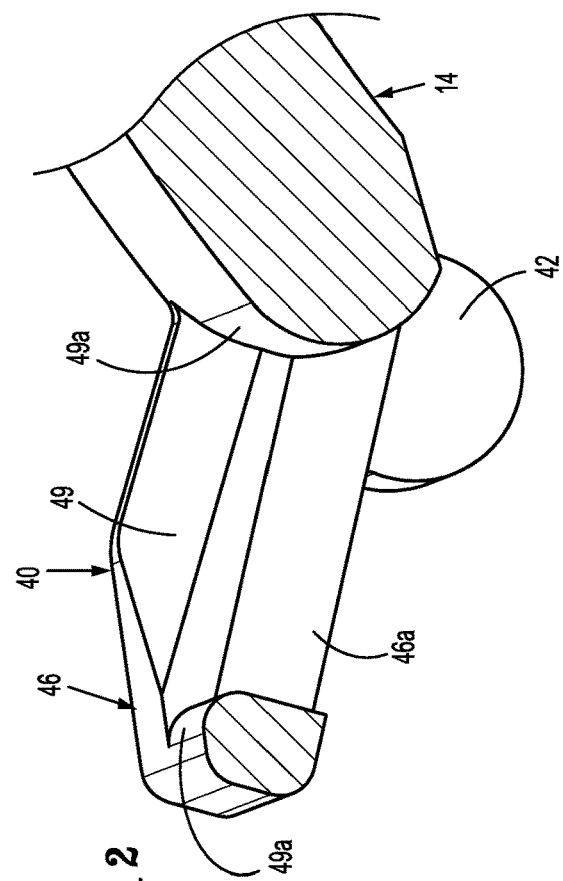
FIG. 1A is a cross-sectional view taken along section line 1A-1A of FIG. 1.
Figure 1:
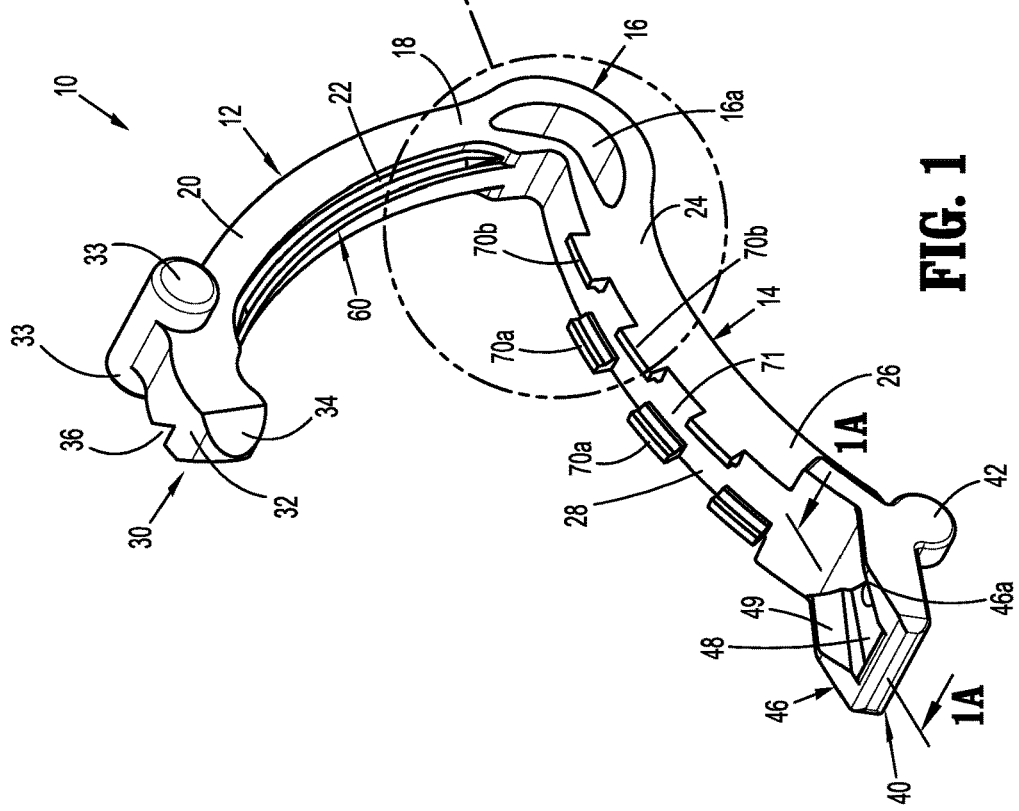
FIG. 1 is a side perspective view of an exemplary embodiment of the presently disclosed polymeric ligation clip in an open position.

The presently disclosed ligation clip will now be described in detail with reference to the drawings in which like reference numerals designate identical or corresponding elements in each of the several views. It is to be understood that the disclosed embodiments are merely exemplary of the disclosure and may be embodied in various forms. Well-known functions or constructions are not described in detail to avoid obscuring the present disclosure in unnecessary detail. Specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
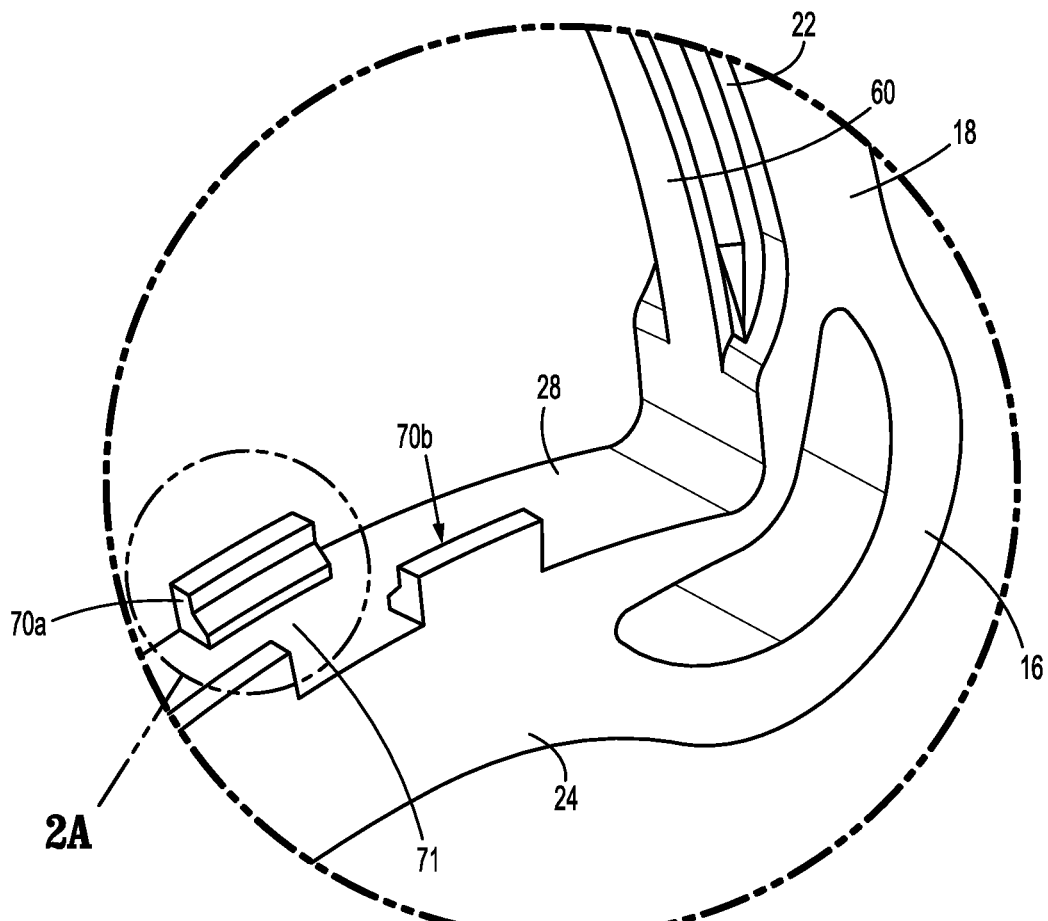
FIG. 2 is an enlarged view of the indicated area of detail shown in FIG. 1.
Figure 2A:
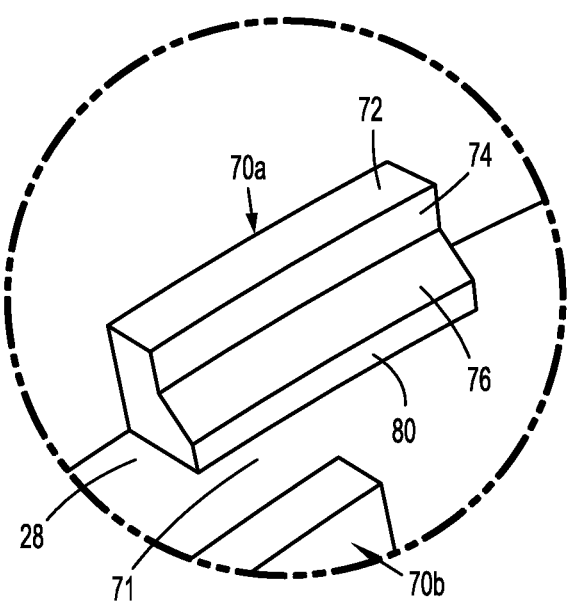
FIG. 2A is an enlarged view of the indicated area of detail shown in FIG. 2.
Figure 3:
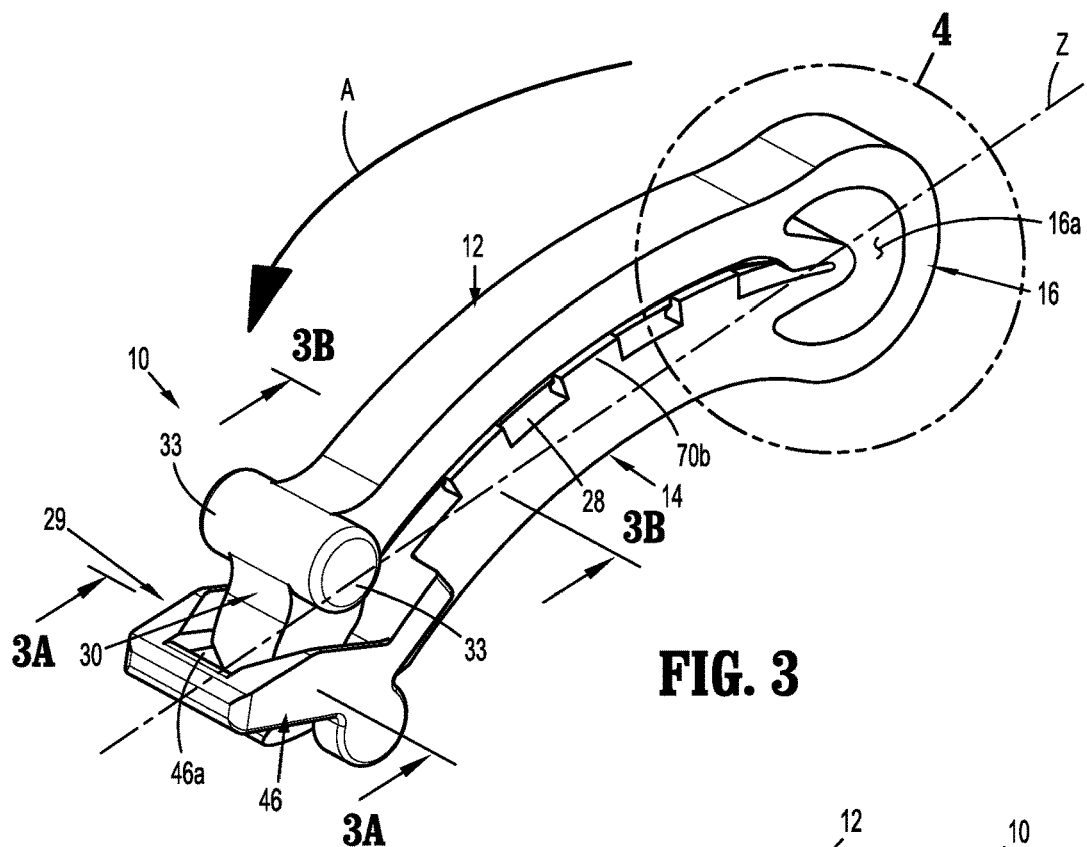
FIG. 3 is a side perspective view of the ligation clip shown in FIG. 1 in the clamped position.

Referring to FIGS. 1-3B, an exemplary embodiment of the presently disclosed polymeric ligation clip is shown generally as ligation clip 10. The ligation clip 10 defines a longitudinal axis "Z" (FIG. 3) and includes a first jaw 12, a second jaw 14, and a hinge portion 16 coupling the first jaw 12 to the second jaw 14. The first jaw 12 is pivotable in relation to the second jaw 14 about the hinge portion 16 to move the ligation clip 10 between an open position (FIG. 1) and a clamped position (FIG. 3). In embodiments, the first and second jaws 12, 14 are curved along the longitudinal axis "Z" (FIG. 3) although other jaw configurations are envisioned. In embodiments, the hinge portion 16 may be integrally formed with the first and second jaws 12, 14, e.g., a living hinge, and may define a crescent shaped through bore 16a to facilitate movement of the first jaw 12 in relation to the second jaw 14 between the open and clamped positions. The through bore 16a also allows for substantially complete closure of the proximal portions of the first and second jaws 12, 14.

The first jaw 12 includes a proximal portion 18, a distal portion 20, and a clamping surface 22. The second jaw 14 includes a proximal portion 24, a distal portion 26, and a clamping surface 28. The proximal portions 18, 24 of the first and second jaws 12, 14, respectively, are coupled to the hinge portion 16.

The distal portion 20 of first jaw 12 includes a first locking element 30 and spaced bosses 33. The first locking element 30 forms a first part of a latching mechanism 29 (FIG. 3) of the ligation clip 10 and includes a head 32 that extends downwardly from the tissue clamping surface 22. In embodiments, the head 32 includes a distal end defined by tapered surfaces 34 and a sidewall having a notch 36 spaced proximally of the tapered surfaces 34. In some embodiments, the notch 36 may be triangular in shape. In certain embodiments, the head 32 may have a rectangular cross-sectional shape. Alternately, other configurations are envisioned. The latching mechanism 29 (FIG. 3) is configured to retain the ligation clip 10 in the clamped position as described in further detail below. In embodiments, the bosses 33 define ends of a cylindrical member supported on the first jaw 12. The bosses 33 are positioned and configured to engage the jaws of an applicator (not shown) to facilitate placement of the ligation clip 10 on tissue and are not described in further detail herein.

Figure 3A:
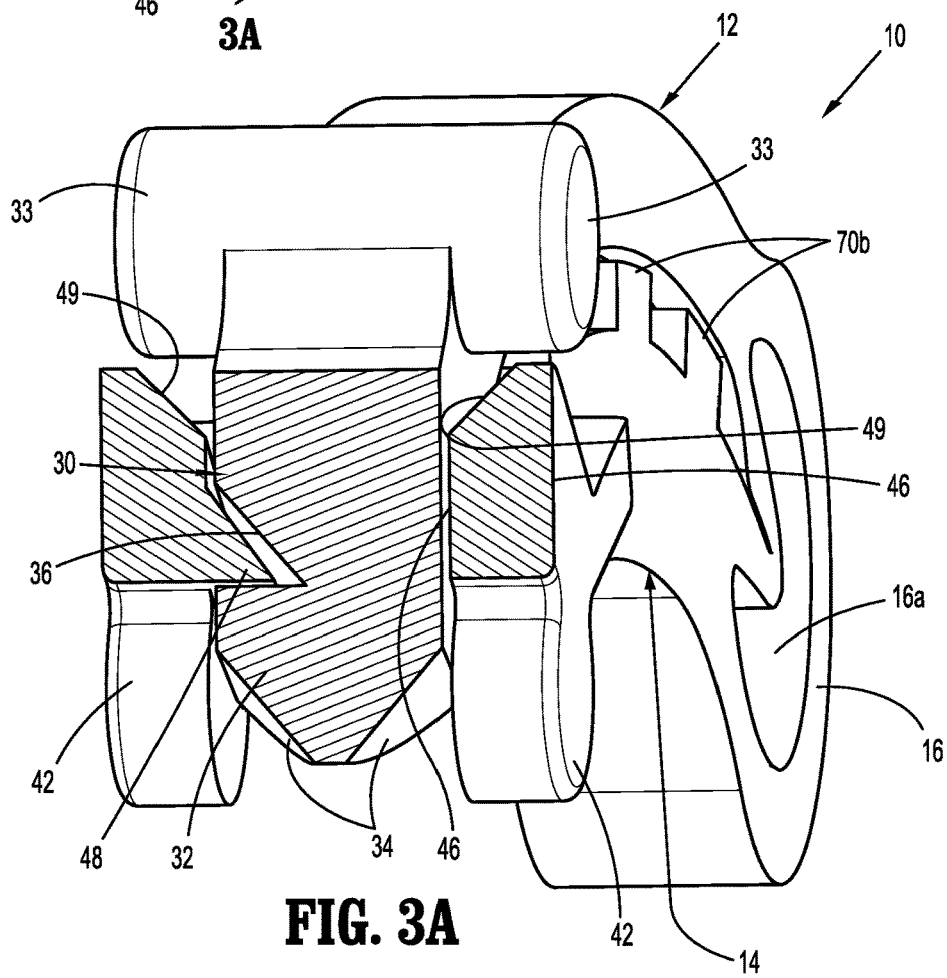
FIG. 3A is a cross-sectional view taken along section line 3A-3A of FIG. 3.

The distal portion 26 of the second jaw 14 includes a second locking element 40 and spaced bosses 42. The second locking element 40 forms a second part of the latching mechanism 29 (FIG. 3.) In embodiments, the second locking element 40 includes a box-like structure 46 that defines a through bore 46a and includes a locking tab 48 that extends into the through bore 46a of the box-like structure 46. The through bore 46a is dimensioned to receive the head 32 of the first locking element 30 when the ligation clip 10 is moved from the open position (FIG. 1) to the clamped position (FIG. 3A). As the head 32 is received within the through bore 46a, the locking tab 48 is received within the notch 36 in the side wall of the first locking element 30 of the first jaw 12 to secure the ligation clip 10 in the clamped position. In embodiments, the through bore 46a defined by the box-like structure 46 of the second locking element 40 is rectangular in shape and is defined by angled walls side walls 49 and radiused proximal and distal walls 49a (FIG. 1A). The side walls 49 and the proximal and distal walls are configured to guide the head 32 of the first locking element 30 into the through bore 46a. The bosses 42 are similar to the bosses 33 of the first jaw 12 and are configured to engage jaws of an applicator (not shown) to facilitate application of the ligation clip 10 to tissue.

The first clamping surface 22 is substantially flat and supports a stepped longitudinal rib 60 (FIG. 3B) having opposite side walls 60a, 60b. Each of the side walls 60a, 60b of the stepped longitudinal rib 60 is defined by a substantially vertical side wall portion 62, an angled side wall portion 64, and vertical side wall portions 66. The vertical side wall portions 62 are contiguous with and extend outwardly from the first clamping surface 22 of the first jaw 12. The angled side wall portions 64 interconnect the vertical side wall portions 62 to the vertical side wall portions 66. The vertical side wall portions 66 are connected by a tissue engaging surface 66a of the longitudinal rib 60 that is in opposition with the clamping surface 28 of the second jaw 14 when the ligation clip 10 is in the clamped position. In embodiments, the stepped longitudinal rib 60 is rectangular and has a first width adjacent the clamping surface 22 and a second width adjacent the tissue engaging wall 66a that is smaller than the first width. In embodiments, the tissue engaging surface 66a of the longitudinal rib 60 is substantially flat and extends substantially the entire length of the tissue clamping surface 22. Alternately, it is envisioned that the longitudinal rib 60 may include one or more longitudinal rib sections that are longitudinally spaced from each other and extend over a length less than the entire length of the tissue clamping surface 22, e.g., 50-80 percent of the length of the tissue clamping surface 22. It is also envisioned that the surface 66a of the stepped longitudinal rib 60 need not be flat but could be curved, ribbed, knurled, or otherwise configured to grip or retain tissue.

The second clamping surface 28 is substantially flat and supports a first row of protrusions 70a and a second row of protrusions 70b. Each of the protrusions 70a of the first row of protrusions 70a is spaced from but longitudinally aligned with each of the other protrusions 70a along a first side of the second clamping surface 28. Similarly, each of the protrusions 70b of the second row of protrusions 70b is longitudinally aligned with each of the other protrusions 70b along a second side of the second clamping surface 28. The protrusions 70a, 70b may have a width that is less than half the width of the clamping surface 28 to define an unobstructed central channel 71 between the first and second rows of protrusions 70a, 70b on the second clamping surface 28. The central channel 71 is dimensioned to receive the stepped longitudinal rib 60 when the ligation clip 10 is in the clamped position. In embodiments, each of the protrusions 70a on the first side of the clamping surface 28 are longitudinally offset from the each of protrusions 70b positioned on the other side of the clamping surface 28 such that the protrusions 70a and 70b are alternatingly positioned on opposite sides of the clamping surface 28 along the length of the clamping surface 28.

Referring to FIGS. 2-3C, each of the protrusions 70a, 70b includes a tissue engaging surface 72 and an inner side wall 73. The tissue engaging surface 72 is positioned in opposition to the clamping surface 22 of the first jaw 12 when the ligation clip 10 is in the clamped position. The inner side wall 73 of each of the protrusions 70a, 70b is positioned in opposition to the one of the side walls 60a, 60b of the stepped longitudinal rib 60 when the ligation clip 10 is in the clamped position (FIG. 3B).

The inner side wall 73 of each of the protrusions 70a, 70b of the first and second rows of protrusions 70a, 70b has a first substantially vertical wall portion 74 that is contiguous with the tissue engaging surface 72 and an angled wall portion 76 that extends from the vertical wall portion 74 towards the clamping surface 28 of the second jaw 14. In some embodiments, the inner side wall 73 of the protrusions 70a, 70b also include a second substantially vertical wall portion 80 that extends between the angled wall portion 76 and the clamping surface 28. The vertical portions 74 of the protrusions 70a, 70b are positioned to align with vertical side wall portions 62 of the stepped longitudinal rib 60 when the ligation clip 10 is in the clamped position and the angled wall portion 76 of the protrusions 70a, 70b are positioned to align with the angled wall portion 64 of the longitudinal rib 60 of the first jaw 12 when the ligation clip 10 is in the clamped position. In addition, the vertical wall portions 80 of the protrusions 70a, 70b are positioned to align with the side wall portions 66 of the stepped longitudinal rib 60 of the first jaw 12 when the ligation clip 10 is in the clamped position.

Figure 4:
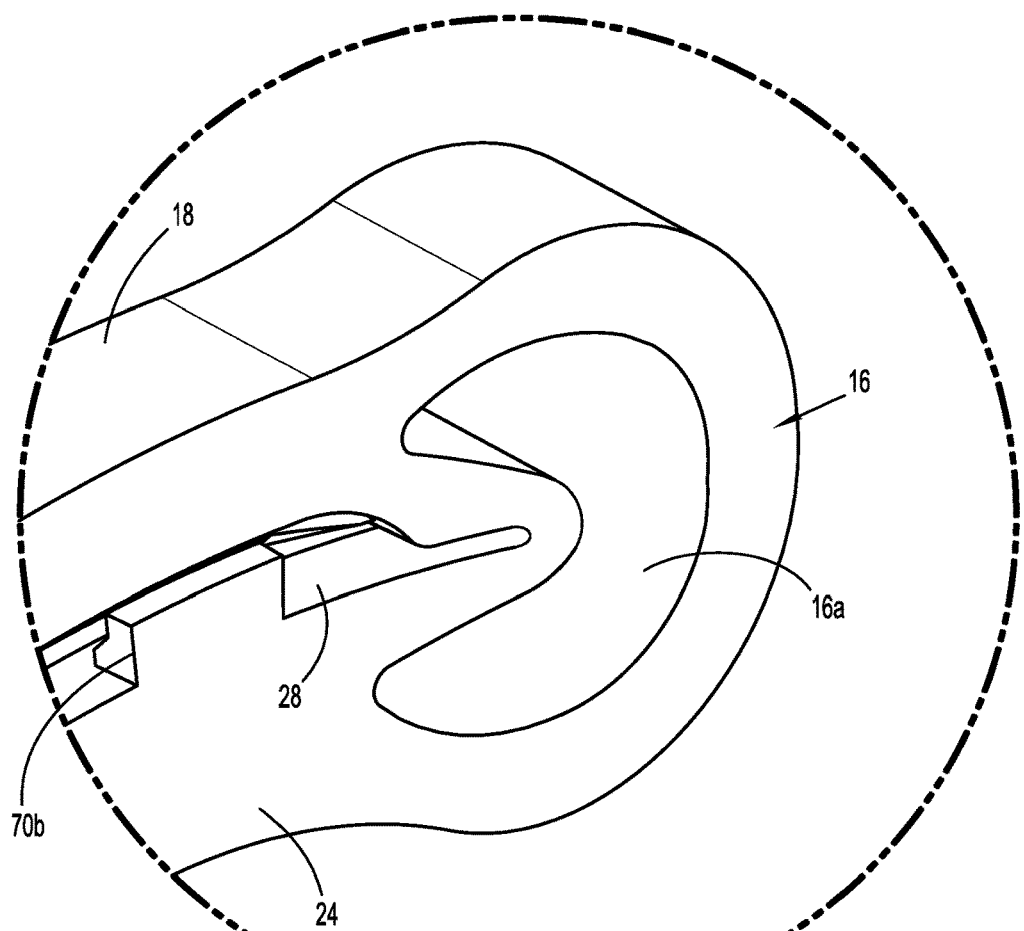
FIG. 4 is an enlarged view of the indicated area of detail shown in FIG. 3.

Referring to FIGS. 3A-4, when the first jaw 12 and the second jaw 14 are moved from the open position (FIG. 1) to the clamped position (FIG. 3) in the direction indicated by arrow A in FIG. 3, the first jaw 12 pivots in relation to the second jaw 14 about the hinge 16 to move the head 32 of the first locking element 30 through the through bore 46a of the box-like structure 46 of the second locking element 40 to secure the ligation clip 10 in the clamped position. As the head 32 of the first locking element 30 approaches the box-like structure 46, the tapered walls 49 and the radiused walls (FIG. 1A) defining the through bore 46a guide the head 32 of the first locking element 30 into the through bore 46a such that the locking projection 48 is received within the notch 36 in the side wall of the head 32 of the first locking element 30. In the clamped position, the stepped longitudinal rib 60 on the clamping surface 22 of the first jaw 12 is received in the central channel 71 defined between the first and second rows of protrusions 70a, 70b on the clamping surface 28 of the second jaw 14. As shown in FIG. 3A, in the clamped position, the protrusions 70a and 70b are longitudinally offset from each other such that the protrusions 70a, 70b are alternatingly space on opposite sides of the ligation clip 10 along the clamping surfaces 22, 28 of the first and second jaws 12, 14.

In embodiments, the surgical ligation clip 10 may be made, in whole or in part, of a resilient bioabsorbable and/or biocompatible polymeric material. Examples of suitable bioabsorbable and/or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The clip may also be made of a polymer material or materials in combination with radiolucent metal alloys. Alternately, other materials may be used to form the clip 10 including biocompatible metals, plastics and composites.

Figure 5:
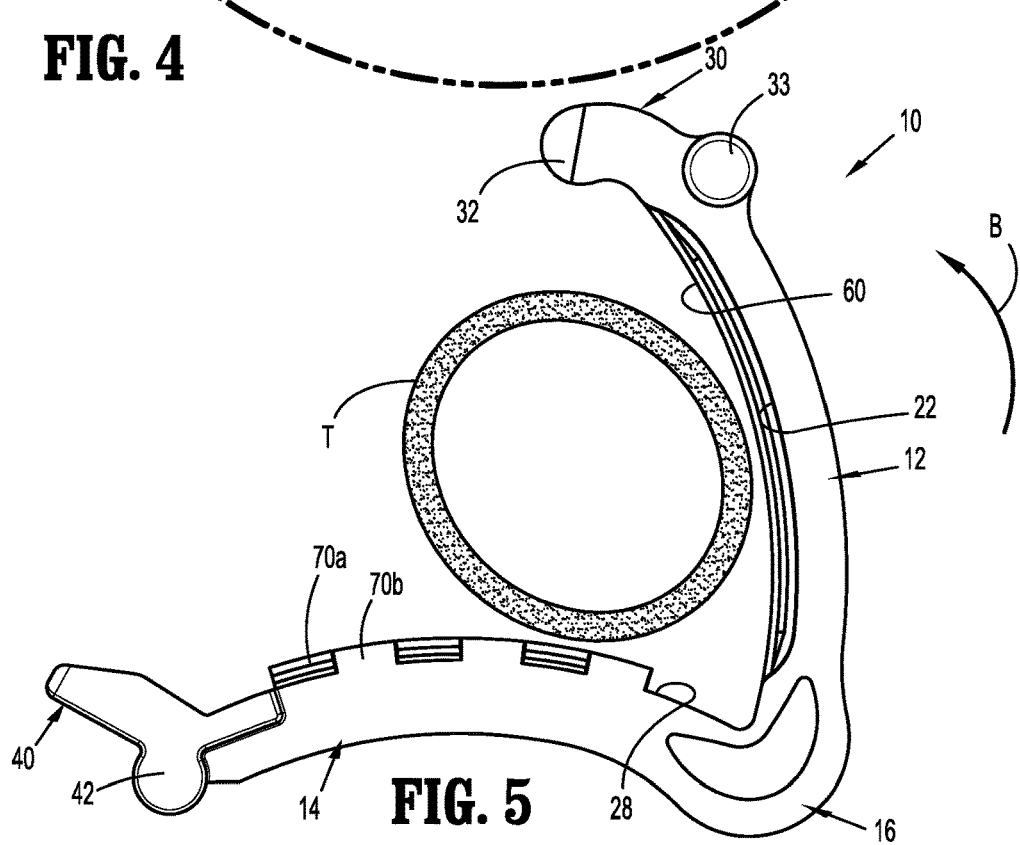
FIG. 5 is a side view of the ligation clip shown in FIG. 1 in the open position placed about tissue.
Figure 6:
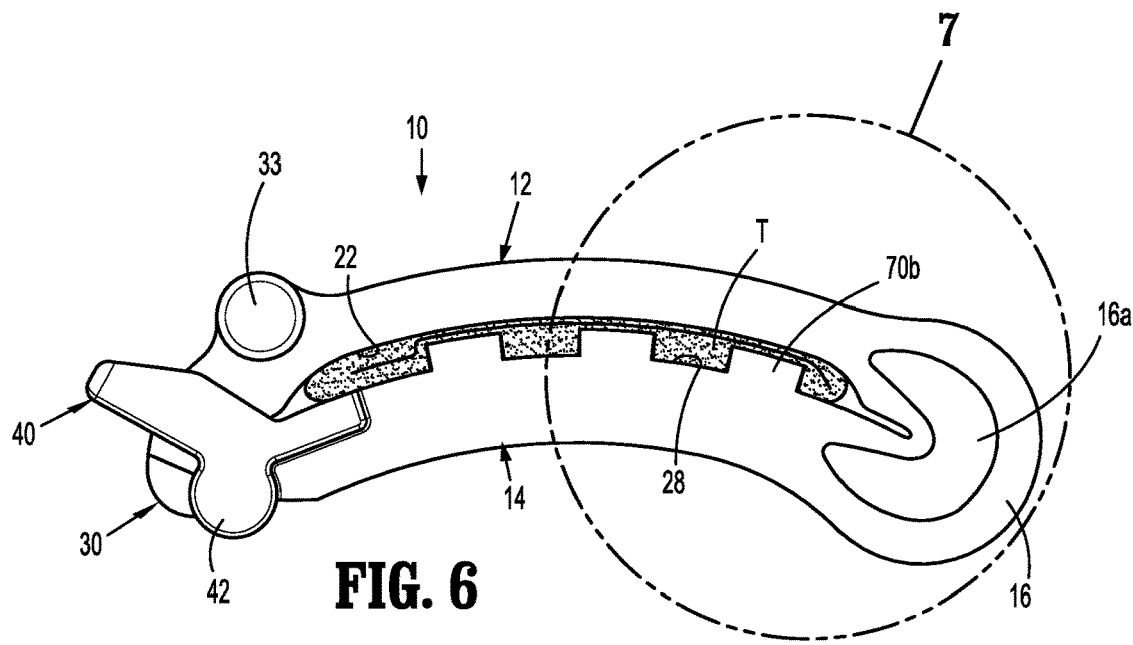
FIG. 6 is a side view of the ligation clip shown in FIG. 5 in the clamped position placed about tissue.
Figure 7:
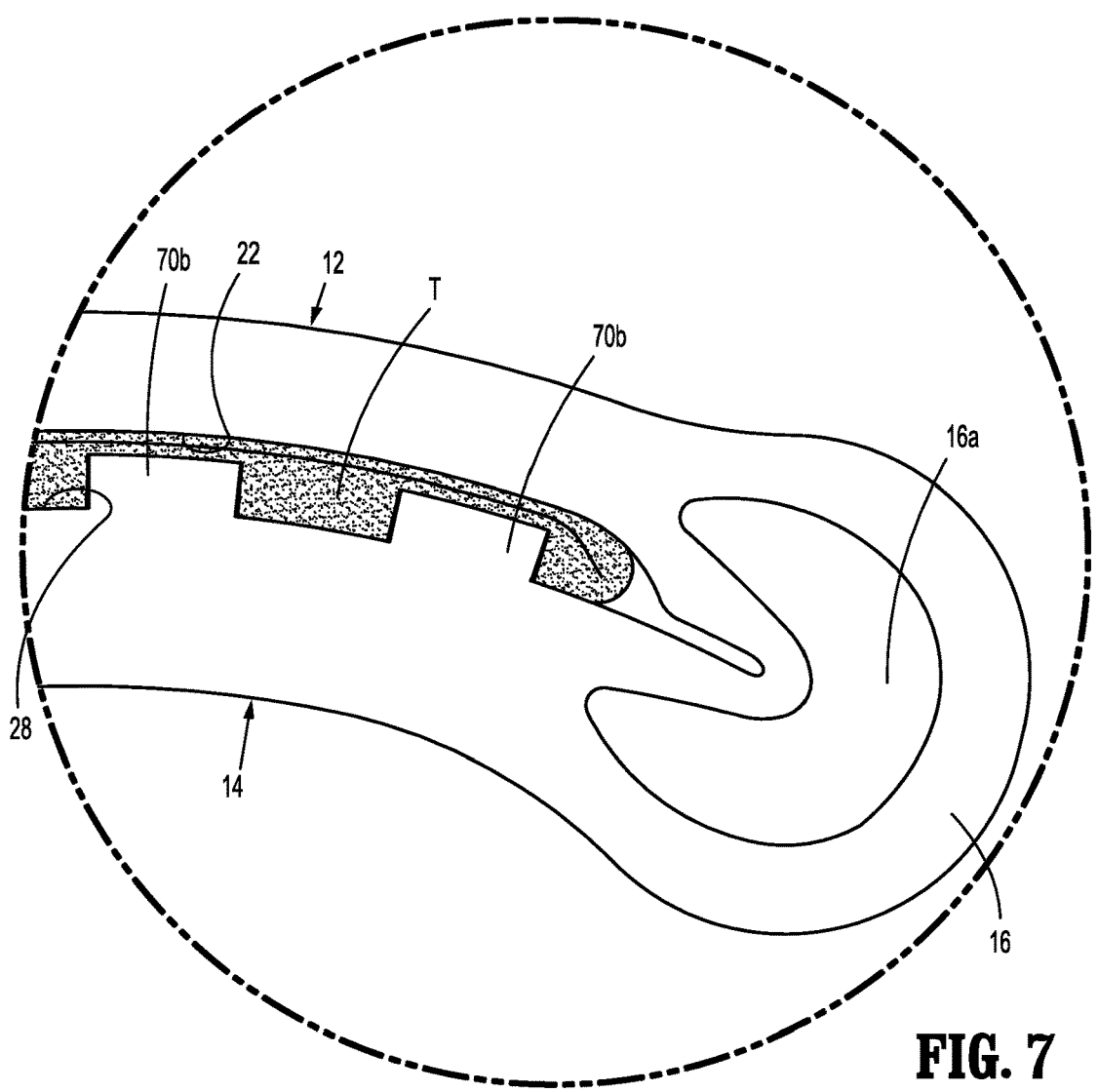
FIG. 7 is an enlarged view of the indicated area of detail shown in FIG. 6.

Referring to FIGS. 5-7, in use, the ligation clip 10 is positioned about tissue "T", e.g., vasculature, such that the tissue "T" is positioned between the tissue clamping surface 22 of the first jaw 12 and the tissue clamping surface 28 of the second jaw 14. As described above, when the ligation clip 10 is moved from the open position (FIG. 5) to the closed position (FIG. 6) in the direction indicated by arrow "B" in FIG. 5, the first jaw 12 pivots in relation to the second jaw 14 about the hinge 16 to move the projection 32 of the first locking element 30 into box-like structure 46 of the second locking element 40. As the projection 32 passes through the through bore 46a of the box-like structure 46, the locking tab 48 of the second locking element 40 is deformed and subsequently snaps into the notch 36 of the first locking element 30 to secure the ligation clip 10 in the clamped position. In embodiments, the notch 36 and the locking tab 48 define right-triangles which are configured to resist unlatching of the ligation clip 10 (FIG. 3A).

Referring to FIG. 7, in the clamped position, the tissue "T" is compressed between the first and second clamping surfaces 22, 28 of the first and second jaws 12, 14, respectively. More particularly, when the ligation clip 10 is moved to the clamped position, the tissue "T" is compressed between the tissue engaging surfaces 72 of the protrusions 70a, 70b and the clamping surface 22 of the first jaw 12, between the angled wall portions of the protrusions 70a, 70b and the angled side wall portion 64 of the longitudinal rib 60, and between the tissue engaging surface 66a of the longitudinal rib 60 and the clamping surface 22 of the first jaw 12.

The above described ligation clip 10 including a first jaw 12 having a stepped longitudinal rib 60 and a second jaw 14 including first and second rows of protrusions 70a, 70b that are in opposition to the longitudinal rib in the clamped position of the ligation clip 10 improve the retention forces of the ligation clip 10 on the tissue "T". In addition, the latching mechanism 29 including the notched head 32 on the first jaw 12 and the locking tab 48 on the second jaw 14 securely fastens the ligation clip 10 onto tissue "T". The combination of the retention structure and latching structure on the first and second jaws 12, 14 minimizes the likelihood that the ligation clip 10 will slide in a direction parallel to the clamping surfaces 22, 28 of the first and second jaws 12, 14, respectively, after the ligation clip 10 has been clamped about the tissue "T".

Figure 8:
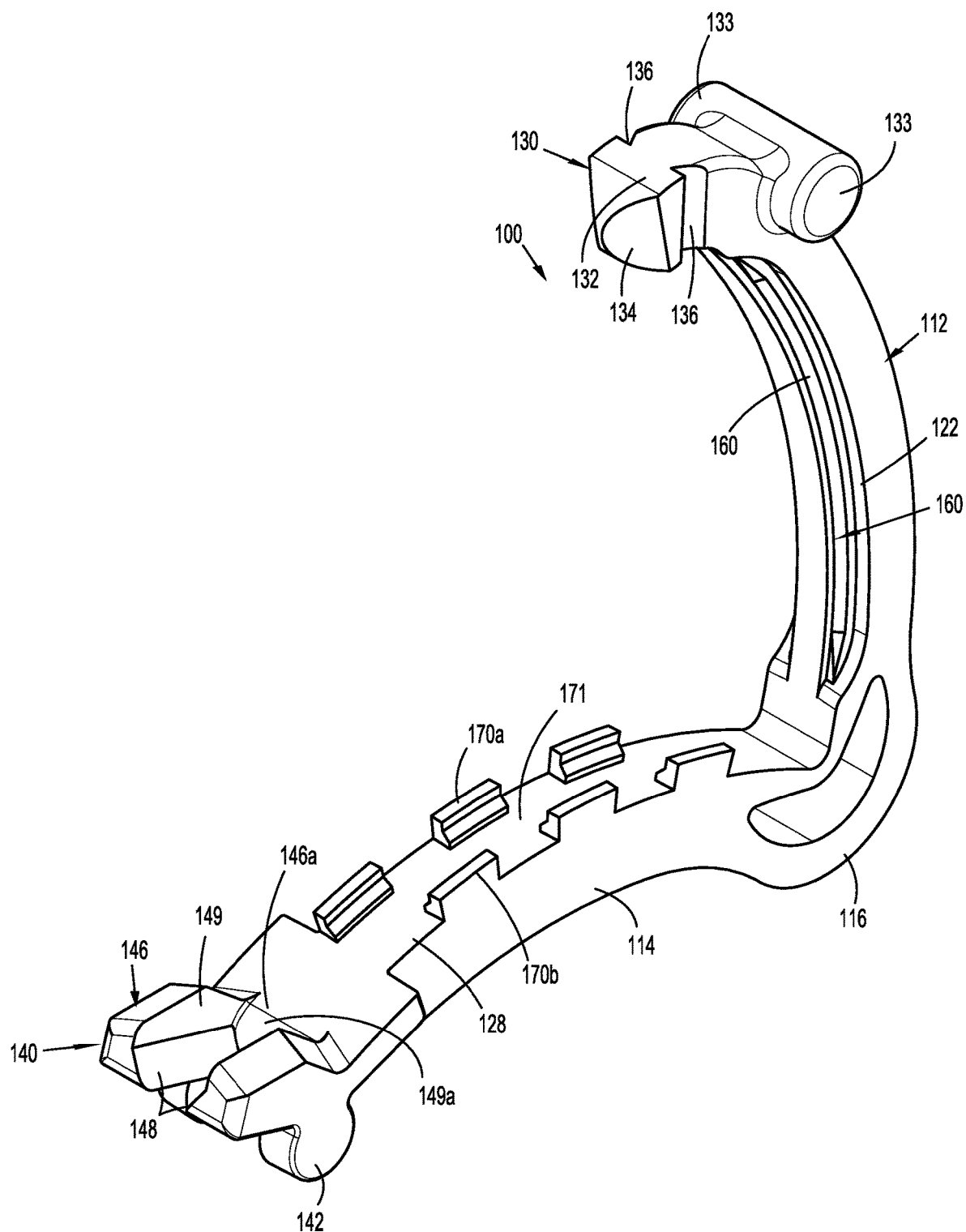
FIG. 8 is a side perspective view of another exemplary embodiment of the presently disclosed polymeric ligation clip in an open position.
Figure 9:
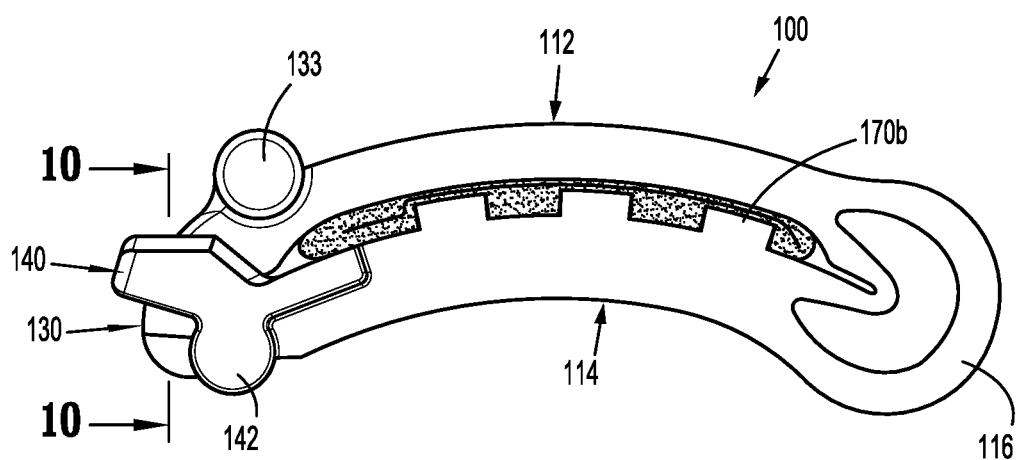
FIG. 9 is a side view of the ligation clip shown in FIG. 8 in the clamped position placed about tissue.
Figure 10:
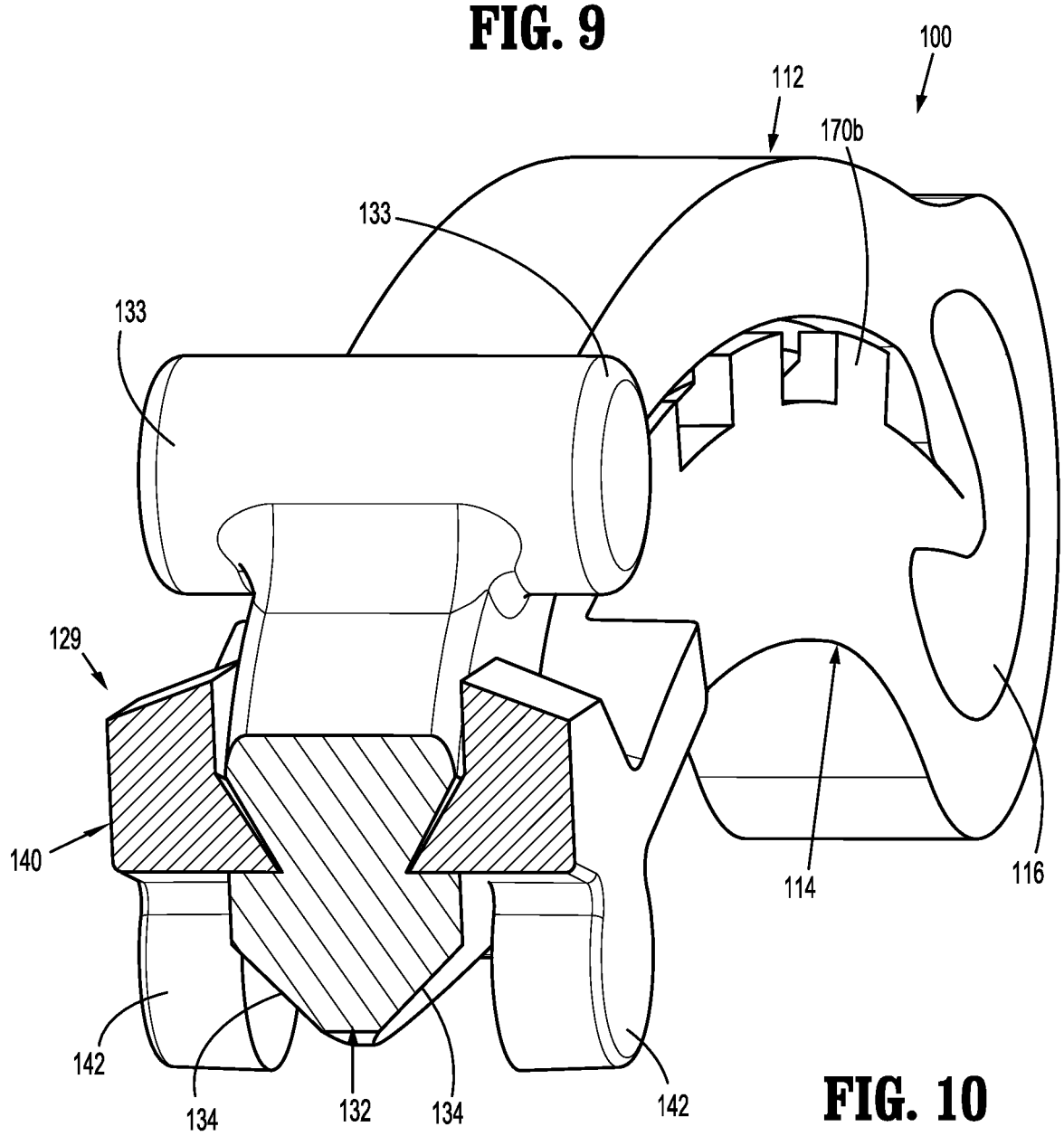
FIG. 10 is a cross-sectional view taken along section line 10-10 of FIG. 9.

FIGS. 8-10 illustrate another exemplary embodiment of the presently disclosed ligation clip shown generally as ligation clip 100. Ligation clip 100 is similar to ligation clip 10 in most respects and includes a first jaw 112, a second jaw 114 and a hinge portion 116. The first jaw 112 includes a clamping surface 122 that supports a longitudinal rib 160. The second jaw 114 includes a clamping surface 128 that supports a first row of projections 170a positioned along a first edge of the clamping surface 128 and a second row of projections 170b positioned along an opposite side of the clamping surface 128. The first and second rows of projections 170a, 170b define a central channel 171 that is dimensioned to receive the longitudinal rib 160 of the first jaw 12 when the ligation clip 100 is in a clamped position. The first and second jaws 112, 114 support bosses 133, 142, respectively. These features are substantially as described above in regard to the ligation clip 10 and will not be described in further detail herein.

The ligation clip 100 differs from the ligation clip 10 (FIG. 1) in that the latching mechanism 129 is modified. More particularly, the first jaw 112 includes a first locking element 130 that includes a head 132 that extends downwardly from the tissue clamping surface 122. In embodiments, the head 132 includes a distal end defined by tapered surfaces 134 and side walls including diametrically opposed notches 136 that are spaced proximally of the tapered surfaces 134. In some embodiments, the notches 136 may be triangular in shape. In certain embodiments, the head 132 may have a rectangular cross-sectional shape. Alternately, other notch and protrusion configurations are envisioned.

The second jaw 114 includes a second locking element 140 that forms a second part of the latching mechanism 129 (FIG. 10.) The second locking element 140 includes a box-like structure 146 that defines an open ended through bore or channel 146a and includes two locking tabs 148 that extend into the channel 146a of the box-like structure 146. The channel 146a is dimensioned to receive the head 132 of the first locking element 130 when the ligation clip 100 is moved from the open position (FIG. 8) to the clamped position (FIG. 10) such that the locking tabs 148 are received within the notches 136 formed in the side walls of the first locking element 130 of the first jaw 112 to secure the ligation clip 100 in the clamped position. In embodiments, the channel 146a defined by the box-like structure 146 of the second locking element 40 is rectangular in shape and is defined by side walls 149 and a proximal wall 149a. In some embodiments, the distal end of the box-like structure 146 is open. As discussed above, the side walls 149 and the proximal wall 149a may be configured to guide the head 132 of the first locking element 130 into the through bore 146a. The latching mechanism 129 (FIG. 10) is configured to retain the ligation clip 100 in the clamped position as described above in regard to ligation clip 10 (FIG. 3A). In embodiments, the notches 136 and the locking tabs 148 define right-triangles that resist unlatching of the ligation clip 100.

Figure 11:
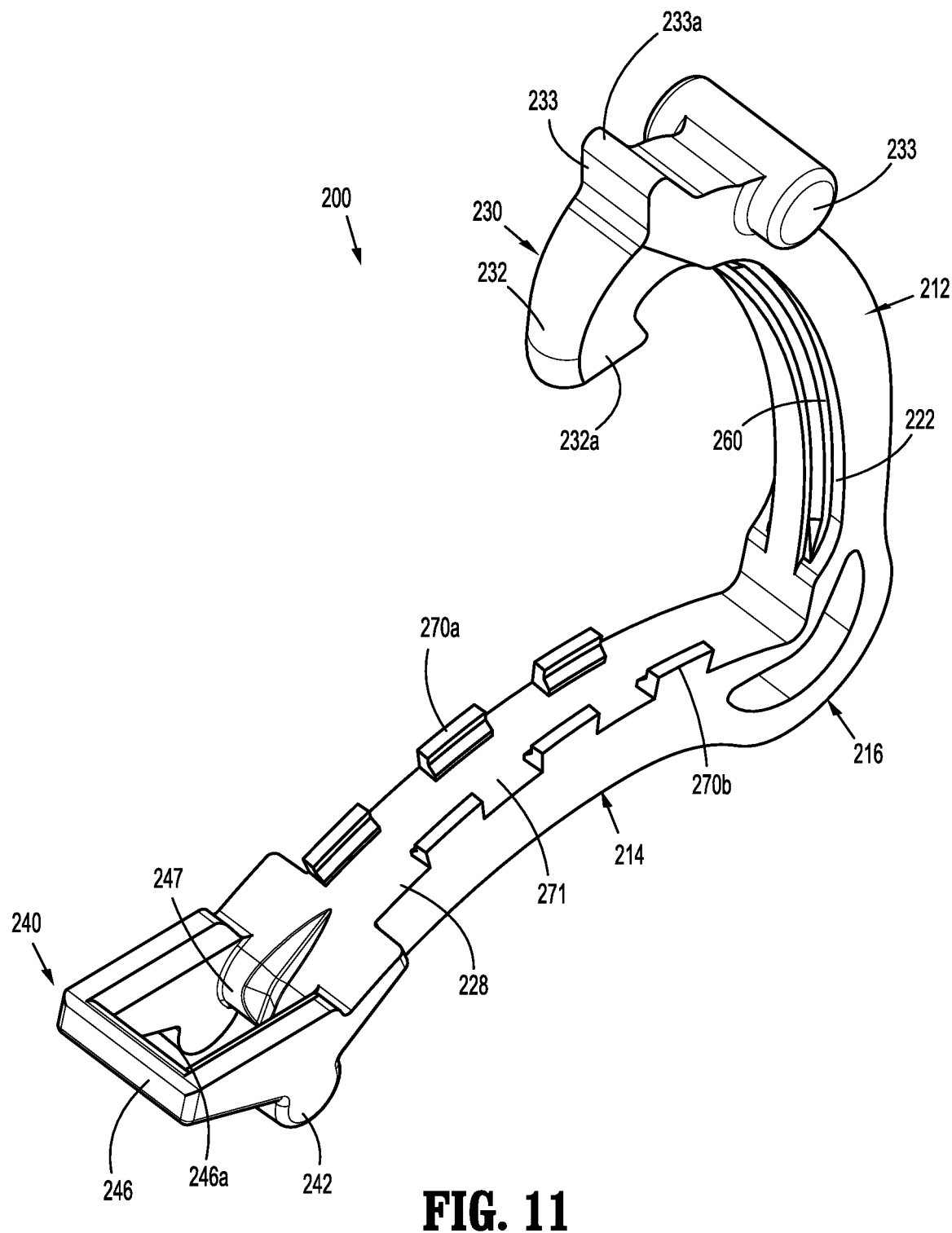
FIG. 11 is a side perspective view of another exemplary embodiment of the presently disclosed polymeric ligation clip in an open position.
Figure 12:
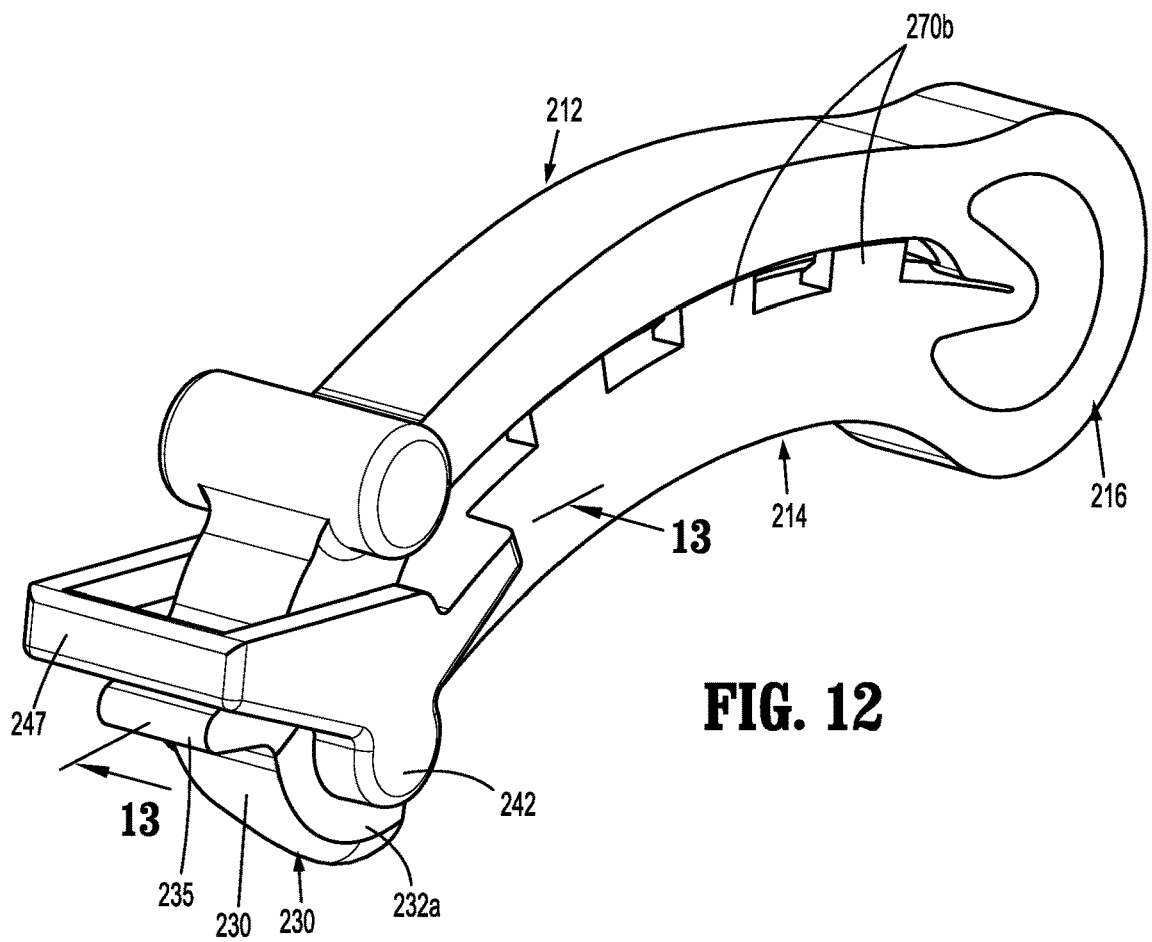
FIG. 12 is a side perspective view of the ligation clip shown in FIG. 11 in the clamped position.
Figure 13:
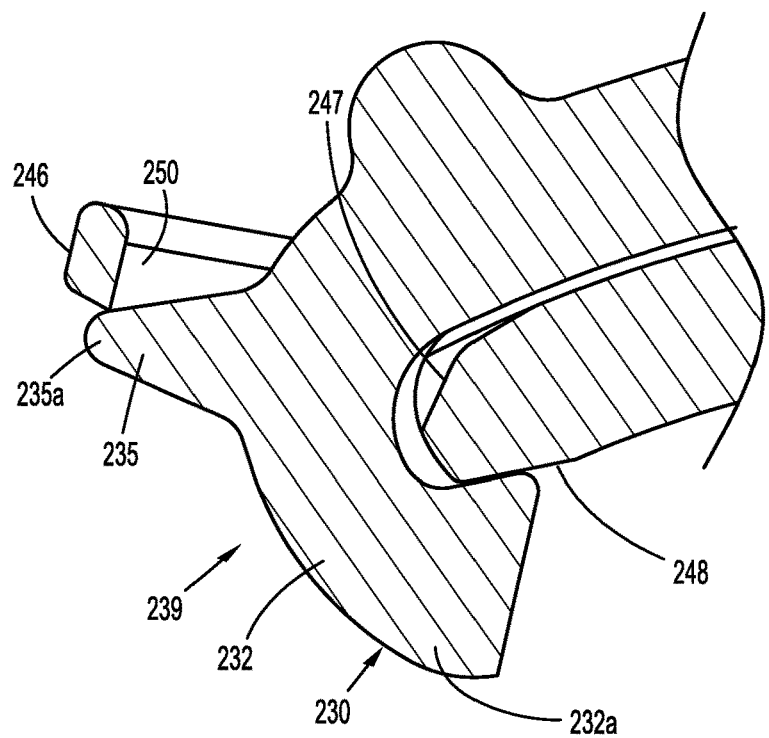
FIG. 13 is a cross-sectional view taken along section line 13-13 of FIG. 12.

FIGS. 11-13 illustrate another exemplary embodiment of the presently disclosed ligation clip shown generally as ligation clip 200. Ligation clip 200 is similar to ligation clip 10 in most respects and includes a first jaw 212, a second jaw 214 and a hinge portion 216. The first jaw 212 includes a clamping surface 222 that supports a longitudinal rib 260. The second jaw 214 includes a clamping surface 228 that supports a first row of projections 270a positioned along a first edge of the clamping surface 228 and a second row of projections 270b positioned along an opposite side of the clamping surface 228. The first and second rows of projections 270a, 270b define a central channel 271 that is dimensioned to receive the longitudinal rib 260 when the ligation clip 200 is in a clamped position. The first and second jaws 212, 214 support bosses 233, 242, respectively. These features are substantially as described above in regard to the ligation clip 10 and will not be described in further detail herein.

The ligation clip 200 differs from the ligation clip 10 (FIG. 1) in that the latching mechanism 239 is modified. More particularly, the first jaw 212 includes a first locking element 230 and the second jaw 214 includes a second locking element 240 that together define the latching mechanism 239. The first locking element 230 includes a head 232 including a hooked portion 232a, and a stop member 235. The stop member 235 has a radiused distal surface 235a. The hooked portion 232 extends downwardly and proximally from the tissue clamping surface 222.

The second locking element 240 includes a box-like structure 246 that defines a through bore 246a, a cam surface 247, and an engagement portion 248 (FIG. 13). The box-like structure 246 includes a distal wall 250. The through bore 246a is dimensioned to receive the hooked portion 232 of the first locking element 230 and the stop member 235 when the ligation clip 200 is moved from an open position (FIG. 11) to a clamped position (FIG. 13). As the ligation clip 200 is moved to the clamped position, the head 232 and the stop member 235 move through the through bore 246a. As the stop member 235 engages the distal wall 250 of the box-like structure 246, the stop member 235 flexes and passes under the distal wall 250 of the box-like structure 246. As the stop member 235 passes under the distal wall 250 of the box-like structure 246, the stop member 235 returns to its undeformed state to a position beneath the distal wall 250 to lock the ligation clip 10 in the clamped position. After the head 232 passes through the box-like structure 246, the hooked portion 232a of the first locking element 230 engages the engagement portion 248 of the second locking element 240 to further secure the ligation clip 200 in the clamped position. In embodiments, the through bore 246a defined by the box-like structure 246 of the second locking element 240 is rectangular in shape and is defined by side walls 249 and a proximal wall 249a. As discussed above in regard to ligation clips 10 and 100, the box-like structure 246 may be configured to direct the hooked portion 232a of the first locking element 230 into engagement with the second locking element 240. The latching mechanism 239 (FIG. 13) is configured to retain the ligation clip 200 in the clamped position as described above in regard to ligation clips 10 and 100 (FIGS. 3A and 10.)

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A ligation clip comprising:
    a first jaw defining a first clamping surface supporting a stepped longitudinal rib, the stepped longitudinal rib extending along at least a portion of the length of the first clamping surface, the stepped longitudinal rib including opposite side walls, each of the opposite side walls including a first angled wall portion and first and second vertical side wall portions that are interconnected by the first angled wall portion; and
    a second jaw defining a second clamping surface, the second jaw being pivotably supported in relation to the first jaw to facilitate movement of the ligation clip from an open position to a clamped position, the second jaw having a first row of protrusions supported on one side of the second clamping surface and a second row of protrusions supported on an opposite side of the second clamping surface, each of the protrusions of the first and second rows of protrusions having an inner side wall in opposition to the stepped longitudinal rib when the ligation clip is in the clamped position, the inner side wall of each of the protrusions including a second angled wall portion and first and second vertical wall portions that are interconnected by the second angled wall portion, the first row of protrusions being laterally spaced from the second row of protrusions to define a channel that extends longitudinally between the first and second rows of protrusions, the channel being positioned to receive the stepped longitudinal rib when the ligation clip is in the clamped position;
    wherein the first angled wall portion of the opposite side walls of the stepped longitudinal rib and the angled side wall portion of the protrusions of the first and second rows of protrusions are positioned to be in opposition to each other in the clamped position.

2. The ligation clip of claim 1, wherein the protrusions in the first row of protrusions are longitudinally aligned and spaced from each other and the protrusions in the second row of protrusions are longitudinally aligned and spaced from each other.

3. The ligation clip of claim 1, wherein each of the protrusions in the first row of protrusions are longitudinally offset from the each of protrusions in the second row of protrusions such that the protrusions are alternatingly positioned on opposite sides of the second clamping surface along the length of the second clamping surface.

4. The ligation clip of claim 1, wherein the first jaw includes a first locking element and the second jaw includes a second locking element, the first locking element being movable into engagement with the second locking element to retain the ligation clip in the clamped position.

5. The ligation clip of claim 4, wherein one of the first or second locking elements includes a head having a distal end and including a first side wall defining a first notch, and the other one of the first or second locking elements includes a box-like structure defining a through bore having a first locking tab extending into the through bore, the first locking tab being positioned to be received within the first notch of the head to retain the ligation clip in the clamped position.

6. The ligation clip of claim 5, wherein the head includes a second side wall defining a second notch and the box-like structure includes a second locking tab that extends into the through bore, the second locking tab being positioned to be received within the second notch of the head to retain the ligation clip in the clamped position.

7. The ligation clip of claim 5, wherein the first notch and the first locking tab have triangular configurations.

8. The ligation clip of claim 5, wherein the box-like structure is rectangular in shape and is defined by angled side walls and a radiused proximal wall that are configured to guide the head into the through bore of the box-like structure.

9. The ligation clip of claim 5, wherein the head has a rectangular cross-sectional shape and the through bore is configured to receive the head.

10. The ligation clip of claim 5, wherein the box-like structure has an open distal end.

11. The ligation clip of claim 4, wherein one of the first or second locking elements includes a head supporting a stop member, the stop member extending outwardly of the head, and the other one of the first or second locking elements includes a box-like structure defining a through bore, the stop member being deformable to facilitate passage of the stop member through the through bore during movement of the ligation clip from the open position to the closed position, the stop member being configured in an undeformed state to engage the box-like structure to obstruct movement of the ligation clip from the clamped position to the open position.

12. The ligation clip of claim 11, wherein the head includes a hooked portion and the other one of the first or second locking elements includes an engagement portion, the hooked portion being positioned to engage the engagement portion to retain the ligation clip in the clamped position.

13. The ligation clip of claim 1, wherein the first vertical side wall portions of the stepped longitudinal rib have a first end contiguous with the first clamping surface and a second end contiguous with the first angled wall portion, and the second vertical wall portion of the inner side wall of each of the protrusions has a first end contiguous with a tissue engaging surface of the respective one of the protrusions and a second end contiguous with the second angled wall portion, the first vertical side wall portions of the stepped longitudinal rib being in opposition to the second vertical wall portions of the protrusions when the ligation clip is in a clamped position.

14. The ligation clip of claim 13, wherein the stepped longitudinal rib includes a second vertical side wall portion that has a first end contiguous with the a tissue engaging surface of the stepped longitudinal rib and a second end contiguous with the first angled wall portion, and the inner side wall of each of the protrusions includes a second vertical wall portion that has a first end contiguous with the second clamping surface of the second jaw and a second end that is contiguous with the second angled wall portion, the second vertical side wall portions of the stepped longitudinal rib being in opposition to the second vertical wall portions of the protrusions when the ligation clip is in a clamped position.

* * * * *